(12) United States Patent
Kramp

(10) Patent No.: US 8,158,210 B2
(45) Date of Patent: Apr. 17, 2012

(54) SYSTEMS AND METHODS FOR TAPE FLAW AND SPLICE AVOIDANCE IN MANUFACTURING

(75) Inventor: Robert A. Kramp, Sumner, WA (US)

(73) Assignee: The Boeing Company, Chicago, IL (US)

( * ) Notice: Subject to any disclaimer, the term of this patent is extended or adjusted under 35 U.S.C. 154(b) by 1862 days.

(21) Appl. No.: 11/261,362

(22) Filed: Oct. 28, 2005

(65) Prior Publication Data
US 2007/0095451 A1    May 3, 2007

(51) Int. Cl.
*B05D 1/26* (2006.01)
(52) U.S. Cl. ........................ 427/427.2; 156/64
(58) Field of Classification Search ........... 427/8, 421.1, 427/427.2; 156/64, 361; 221/1, 73
See application file for complete search history.

(56) References Cited

U.S. PATENT DOCUMENTS

| | | | |
|---|---|---|---|
| 4,176,566 A | 12/1979 | Patterson et al. | |
| 4,547,250 A * | 10/1985 | Murayama | 156/384 |
| 4,583,181 A | 4/1986 | Gerber et al. | |
| 4,867,834 A | 9/1989 | Alenskis et al. | |
| 4,915,771 A * | 4/1990 | O'Brien et al. | 156/574 |
| 4,972,326 A * | 11/1990 | Jung et al. | 702/36 |
| 5,873,392 A | 2/1999 | Meyer et al. | |
| 6,295,129 B1 | 9/2001 | Bjork | |
| 6,725,123 B1 * | 4/2004 | Denuell | 700/122 |
| 6,799,619 B2 | 10/2004 | Holmes et al. | |
| 6,871,684 B2 | 3/2005 | Engelbart et al. | |
| 6,913,662 B2 * | 7/2005 | Barilovits et al. | 156/60 |
| 2003/0145932 A1 * | 8/2003 | Holmes et al. | 156/64 |

* cited by examiner

*Primary Examiner* — George Koch

(57) ABSTRACT

Systems and methods for avoidance of tape flaw or splices in manufacturing are disclosed. In one embodiment, a method of applying a tape onto a workpiece includes feeding the tape from a tape supply using a tape application assembly, and applying the tape onto the workpiece using the tape application assembly. Simultaneously with the feeding of the tape, the tape is monitored for a marker indicating a defect within the tape, the marker being spaced apart along the tape from the defect such that the marker arrives prior to the defect. The method further includes detecting the marker, and avoiding the application of a portion of the tape that includes the defect onto the workpiece.

11 Claims, 7 Drawing Sheets

| CODED MARKER | CODED DATA | |
|---|---|---|
| A | 120 | —362 |
| B | 240 | —364 |
| C | 360 | —366 |
| D | 480 | —368 |
| E | 600 | —370 |
| F | 720,72 | —372 |
| G | 840,192 | —374 |
| H | 960,312 | —376 |
| I | 1080,432 | —378 |
| J | 1200,60,552 | —380 |

| DATA FORMAT: | |
|---|---|
| PLACE IN SERIES | DESCRIPTION |
| 1ST VALUE IN SERIES | DISTANCE TO END OF ROLL |
| 2ND VALUE IN SERIES | DISTANCE TO SPLICE #1 |
| 3RD VALUE IN SERIES | DISTANCE TO SPLICE #2 |
| VALUE IN n+1 SERIES | DISTANCE TO SPLICE #n |

SYSTEMS AND METHODS FOR TAPE FLAW AND SPLICE AVOIDANCE IN MANUFACTURING

FIELD OF THE INVENTION

This invention relates generally to systems and methods for registering and avoiding flaws or splices in rolls of tape, and more specifically, to systems and methods for registering flaws or splices in composite tapes during manufacturing of composite structures.

BACKGROUND OF THE INVENTION

Composite structures are commonly manufactured by progressively building up the structure with a plurality of layers of thin composite tape (or tow) laid one layer upon another. Typically, the operation begins by laying one or more tapes onto a starting template or tool that has a configuration generally corresponding to the desired shape of the article to be produced. A tape placement head of a manufacturing system moves over the surface of the template, guiding the one or more tapes of composite material onto the template. The head usually makes repeated passes over the template in a defined pattern until the composite material is entirely collated, building up successive layers of the composite tape to form the desired workpiece. A compaction roller (or other suitable presser device) is typically used for pressing the tape against the workpiece, thereby facilitating adhesion of the successive layers. The workpiece may then be subjected to a curing process (e.g. heating) to further adhere and bond the composite layers. Conventional systems for forming composite structures using successive layers of tape include those systems disclosed, for example, in U.S. Pat. No. 6,799,619 B2 issued to Holmes et al., and U.S. Pat. No. 6,871,684 B2 issued to Engelbart et al.

Composite tape rolls provided for forming composite structures may contain defective material or tape splices where defective material has been removed by the tape manufacturer. These splices can result in random and unpredictable process interruptions during lay up by a composite tape laying machine, causing down time during which the spliced section of the tape must be removed from the composite structure being manufactured. Additionally, reaching the end the tape roll unexpectedly can cause similar problems. To avoid tape flaws, splices, and roll ends, flaw avoidance systems typically use data provided by tape manufacturers that indicates the location of splices or flaws and roll ends to scrap lengths of tape that contain the splices or flaws, or to stop the process in the case of reaching a roll end. In these systems all such location data are referenced to the tape end at the leader of the tape roll.

Although desirable results have been achieved using such prior art systems, there may be room for improvement. For example, tape length can be lost and become unaccounted for by the flaw avoidance system. This results in a loss of the measuring reference to the starting end of the tape and the inability to avoid tape splices, flaws and/or roll ends until manual adjustments are made. However, these manual adjustments may be inaccurate and can contribute to further inability to avoid tape splices. Novel systems and methods that improve the tracking of tape splices by the flaw avoidance systems would therefore have utility.

SUMMARY OF THE INVENTION

The present invention is directed to systems and methods for avoidance of tape flaw, splices and roll ends in manufacturing, including the manufacturing of composite structures. Embodiments of systems and methods in accordance with the present invention may reduce the inaccuracies in referencing and tracking flaws, splices, and roll ends present in a tape, and may reduce downtime and associated costs, in comparison with the prior art.

In one embodiment of a method in accordance with the invention, during tape manufacture the location of the roll end is known and flaws or splices in a tape are detected. Markers are then provided on the composite tape or on the removable portion(s) of the tape as the tape is wound into a roll by a manufacturer. Each marker holds a parameter or set of parameters that indicates the location of one, or more flaws, or splices and/or the roll end relative to the marker. The markers are positioned in such a way that they are detectable prior to the unwinding of the tape to the flaw, splice or end of roll. During the use of such marked tapes for composite lay up, a tape is unwound and the parameter(s) held by each of the one or more markers is detected. A distance from each marker to the flaw(s), splice(s) and/or roll end is obtained from each parameter. This distance is then compared to the length of a tape course to be laid. If the distance from a marker to a flaw, splice, or roll end is shorter than the length of the tape course to be laid, the flaw or splice is avoided by scrapping the tape at least to a marker beyond a flaw or splice, or the process may be stopped (e.g. in the case of encountering the end of a roll). In a particular embodiment, an alternate tape course that is shorter than the distance between the marker and the flaw, splice or end of roll can be laid before the tape is scrapped to avoid a flaw or splice. In another embodiment of the invention, the markers used to indicate the location of flaws, splices or the roll end are provided on a removable part(s) of the tape. In an additional aspect of the invention, one or more markers are placed at a distance from the flaw or splice that is greater than the longest required tape course used in the manufacture of a part.

In an alternate embodiment, a method of applying a tape onto a workpiece includes feeding the tape from a tape supply using a tape application assembly, and applying the tape onto the workpiece using the tape application assembly. Simultaneously with the feeding of the tape, the tape is monitored for a marker indicating a defect within the tape or the end of the roll, the marker being spaced apart along the tape from the defect or roll end such that the marker arrives prior to the defect or roll end. The method further includes detecting the marker, and avoiding the application of a portion of the tape that includes the defect onto the workpiece or where the end of roll would be encountered before reaching the end of the length of a course of tape.

BRIEF DESCRIPTION OF THE DRAWINGS

Embodiments of the present invention are described in detail below with reference to the following drawings.

DETAILED DESCRIPTION

The present invention relates to systems and methods for avoiding tape flaws or splices in manufacturing, and for encountering and avoiding the end of a tape roll within a partially completed course of tape, including manufacturing of composite structures. Many specific details of certain embodiments of the invention are set forth in the following description and in FIGS. 1-9 to provide a through understanding of embodiments. The present invention may have additional embodiments, or may be practiced without one or more of the details described below.

Generally, embodiments of systems and methods in accordance with the present invention provide advance reference and tracking of tape flaws or splices as a tape is unwound during use for manufacturing. Thus, embodiments of the present invention may advantageously reduce the inaccuracies in referencing and tracking flaws or splices in a tape, and may improve efficiency and reduce costs associated with manufacturing components formed from composite tape.

Figure 1:
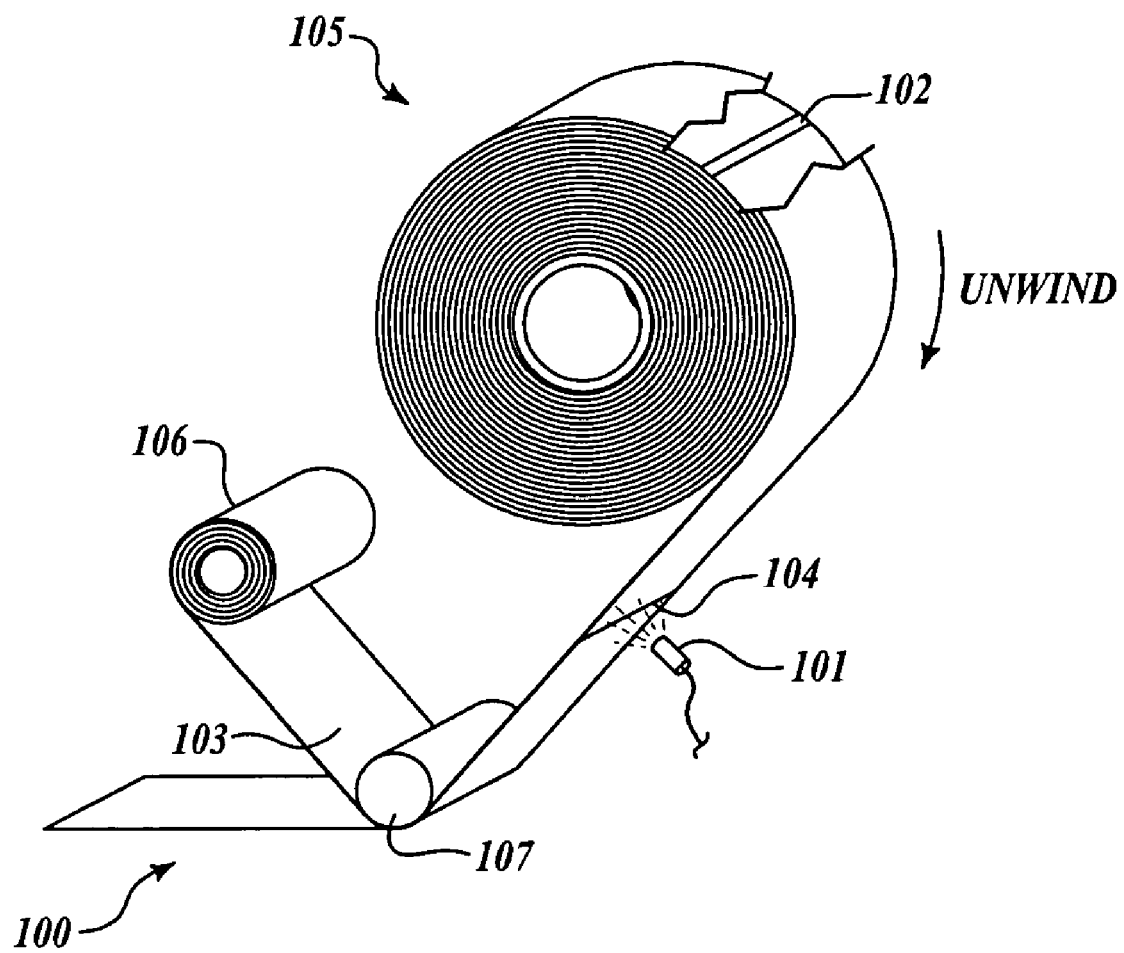
FIG. 1 is an isometric view of a composite tape provided with markers in accordance with an embodiment of the invention.

FIG. 1 is an isometric view of a composite tape 100 provided with markers 104 in accordance with an embodiment of the invention. One or more markers 104 are provided on the composite tape 100 as the tape is wound into a roll. The tape 100 may include fibers, including carbon fibers are any other suitable fibers. The markers 104 are provided at specified distances from a particular flaw or splice 102 (shown in the cutaway portion of FIG. 1), or roll end (not shown) and each marker 104 indicates the location of the flaw or splice 102 (or the roll end) relative to the marker 104. The markers 104 are provided so that as the tape 100 is unwound for use, they can be detected in advance of the flaw or splice 102. The markers 104 may be formed using an ink, a paint, or any other suitable coating or material, and may be any suitable color or opacity that may be detected (visibly or non-visibly) during the unwinding of the roll of tape 100. In some embodiments, the markers 104 are formed using ink and may be applied using an inkjet printer. In further embodiments, the markers 104 may be formed manually using a marking pencil or other suitable device or material. The processes and materials used to form the markers 104 may be selected based on the tape materials and manufacturing process specifications involved in the manufacturing operation.

As further shown in FIG. 1, in this embodiment, a removable backing portion 103 is coupled to the composite tape 100. As the composite tape 100 is unwound from a tape roll 105, it is applied to a workpiece using a pressing device 107, while a take up reel 106 winds up the removable backing portion 103. A sensor 101 monitors the composite tape 100 (or the removable portion 103, or both) for the presence of the marker 104.

In one specific embodiment, one or more markers 104 are placed at a distance from the flaw or splice 102 that is greater than a longest required tape course (e.g. a length of tape sufficient to wind one revolution around a mandrel, or the length of a forming tool, workpiece, or other suitable body or distance). This ensures that an adequate length of the tape 100 sufficient for any tape course is always available.

Figure 2:
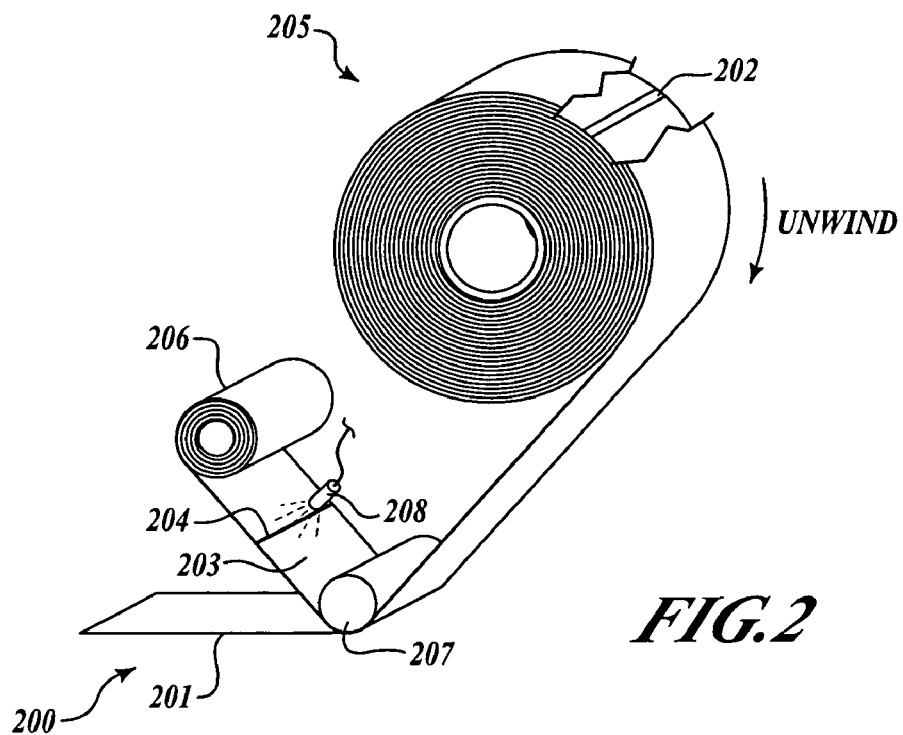
FIG. 2 is an isometric view of an embodiment of a composite tape where the markers are placed on a removable part of the tape.

FIG. 2 is an isometric view of a composite tape 200 in accordance with an alternate embodiment of the invention. In this embodiment, the composite tape 200 includes a composite portion 201 and a removable portion 203. One or more markers 204 are placed on the removable portion 203 (e.g. backing paper) of the composite tape 200, each marker 204 indicating an upcoming location of a splice or flaw 202 (show in the cutaway portion of FIG. 2). The removable portion 203 may be on the side of the tape 200 opposite from the side of the composite portion 201 to be taped down. A pressing device 207 presses against the removable portion 203 to apply the composite portion 201 to a workpiece.

In some embodiments, the composite portion 201 has removable coverings on both sides (e.g. a backing paper on one side and a plastic film layer on the other side). In such cases, the markers 204 may be placed on any of these layers and portions. The markers 204 placed on the removable portion 203 can be detected by a sensor 208 during the application process as the tape 200 unwinds from a tape roll 205 and as the removable portion 203 is collected by a take up reel 206. The sensor 208 can be any suitable sensor for detecting markings, including, for example, a camera, a barcode reader/scanner, or any other suitable sensors. In other particular embodiments, such as the case of marking on the removable portion or portions, the sensor 208 may be chosen depending on the means of marking. For example, metallic tape could be used with metal sensing sensor, photoelectric and photographic sensors could be used for high contrast markers (e.g. black on white, barcode readers used with barcodes etc.). A common barcode or other standard coded marking format may advantageously allow more data to be carried and captured at high speed.

Figure 3:
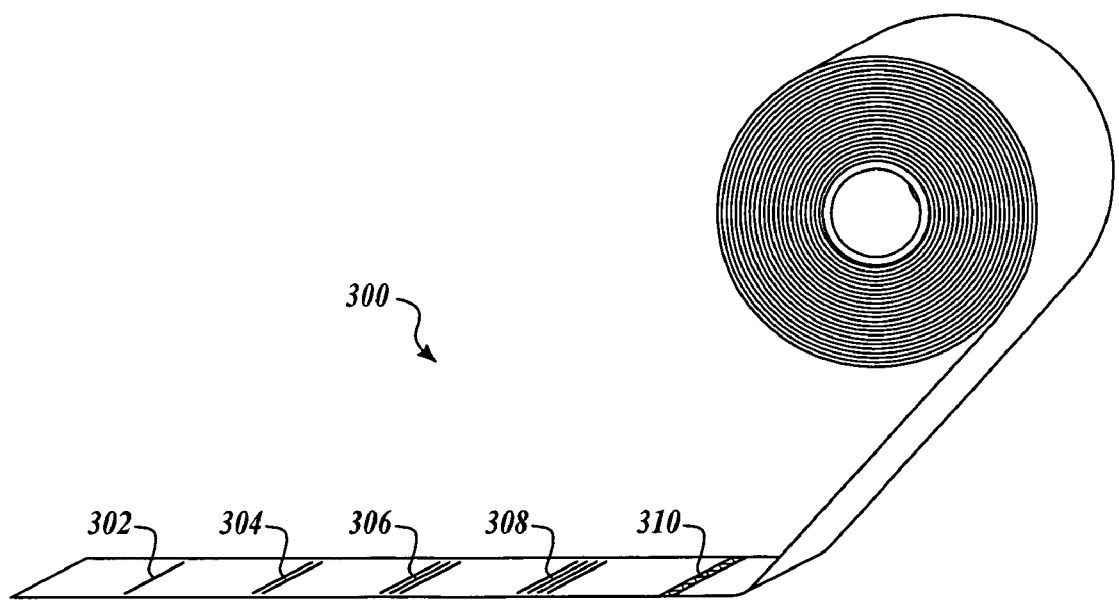
FIG. 3 is an isometric view of a composite tape having multiple line markers in accordance with another embodiment of the invention.

FIG. 3 is an isometric view of a tape roll 300 with one or more markers indicating a flaw or splice. In this embodiment, a first marker is a single line 302, followed by a sequence of additional markers that are groupings of two lines 304, then three lines 306, then four lines 308. These markers are detectable by a sensor. The groupings of lines serve to "count down" the tape length as the machine lay up process dispenses from the roll and the flaw or splice approaches. Each type of line groupings would be set to represent a discrete distance to a flaw or splice location 310. For example, a single line 302 can represent a first distance (e.g. 100 feet) to the flaw or splice 310, double lines 304 can represent a second distance (e.g. 75 feet) to the flaw or splice 310, and triple lines 306 can represent a third distance (e.g. 50 feet) to the flaw or splice 310, and so on and so forth. In alternate embodiments, different types of markers (other than groups of parallel lines) may be used to indicate different distances to the upcoming slice or flaw. For example, the different markers might consist of different line thicknesses, line colors, patterns, symbols, or any other suitable types of markers. The use of more than one different type of marker before a flaw or splice may further reduce the likelihood that lost tape length may result in unreliability of flaw or splice avoidance features.

Figure 4:
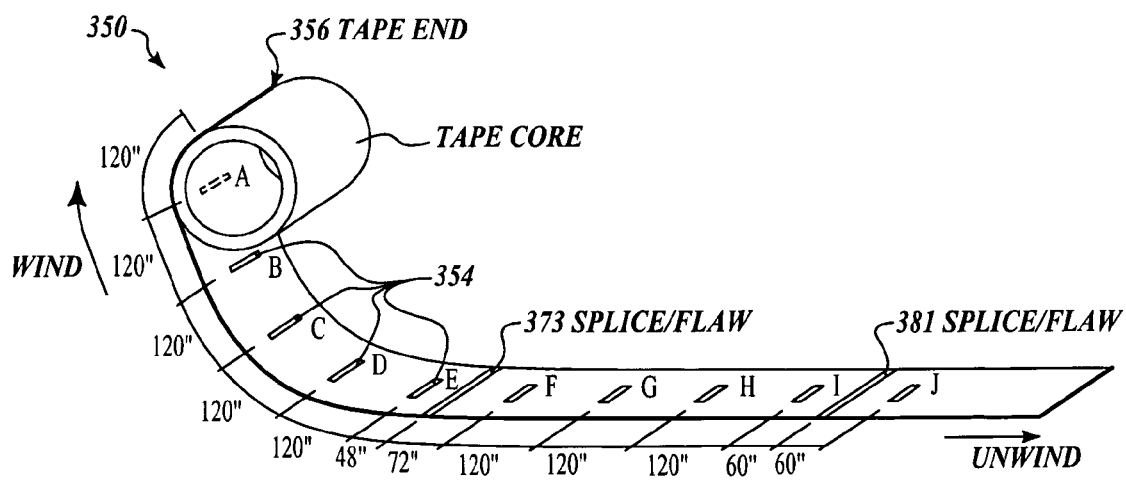
FIG. 4 is an isometric view of a composite tape having coded data markers in accordance with another embodiment of the invention.

In yet another embodiment, a barcode, a data matrix or other similar coded mark that can contain more data than just a marker line may be applied to the removable part of the tape (e.g. backing paper). More specifically, FIG. 4 is an isometric view of a composite tape 350 having coded data markers 354 in accordance with another embodiment of the invention. In this embodiment, some or all of the markers 354 may be located relative to a single reference location, such as the trailing end of the roll 356, and the markers 354 may be spaced at some regular interval from there. By using a marking that can contain more coded information, each marking could contain enough data to represent the cumulative information about locations of all splices, flaws and the roll end that would exist beyond each and every mark read (the word beyond meaning in the direction toward the end of the roll).

More specifically, as shown in a first table 360 in FIG. 4, a first coded marker A provides a first coded data 362 indicating a distance of 120 units to the tape end 356. Similarly, a second, third, fourth and fifth coded markers B, C, D, and E, provide second, third, fourth, and fifth coded data 364, 366, 368, 370 indicating distances to the tape end 356. A sixth coded marker F, however, provides a sixth coded data 372 that indicates both a distance to the tape end 356 (i.e. 720 units) and also another distance to a first splice (or flaw) 373. A seventh, eighth, and ninth coded markers G, H, I, provide seventh, eighth, and ninth coded data 374, 376, 378 which also indicate two distances, specifically a distance to the tape end 356, and another distance to the first splice (or flaw) 373. A tenth coded marker J provides a tenth coded data 380 that indicates a distance to the tape end 356, another distance to the first flaw 373, and yet another distance to a second flaw 381. As shown in a second table 385 (FIG. 4), this pattern of markers 354 and coded data may extend indefinitely along the tape 350.

Each marker 354 may advantageously provide a controller with an updated distance from it to the trailing end of the roll. The markers 354 (or barcodes) themselves would not need to contain the information about splice locations. Since one problem with prior art systems and methods is the fact that accurate reference to the splice location gets lost routinely, embodiments of the present invention may advantageously overcome this problem by providing an accurate position reference to the end of the roll that can be refreshed repeatedly by the reading marker (barcode) position data. Using embodiments of the invention, the flaw avoidance control software can otherwise be very similar to prior art systems and methods so development cost can be minimized. Less data may be required to be contained at each marking in this case and this may make finding a reliable code format easier. Each time that a barcode is read it would send the distance from it to trailing tape end position that is coded into it to the control. Splices/flaws locations would also be defined by their distance from the trailing end but entry of this data would be a separate operation from reading the barcode markings and making the tape position updates. An operator may only need to manually enter or automatically scan the flaw/splice data into the controller one time when the roll is first loaded or if it were reloaded on the tape laying machine. Having the information carried in the markers 354 (barcodes) throughout the length of the tape roll may advantageously allow the controller to find discrete positions within the tape roll with some accuracy.

Figure 5:
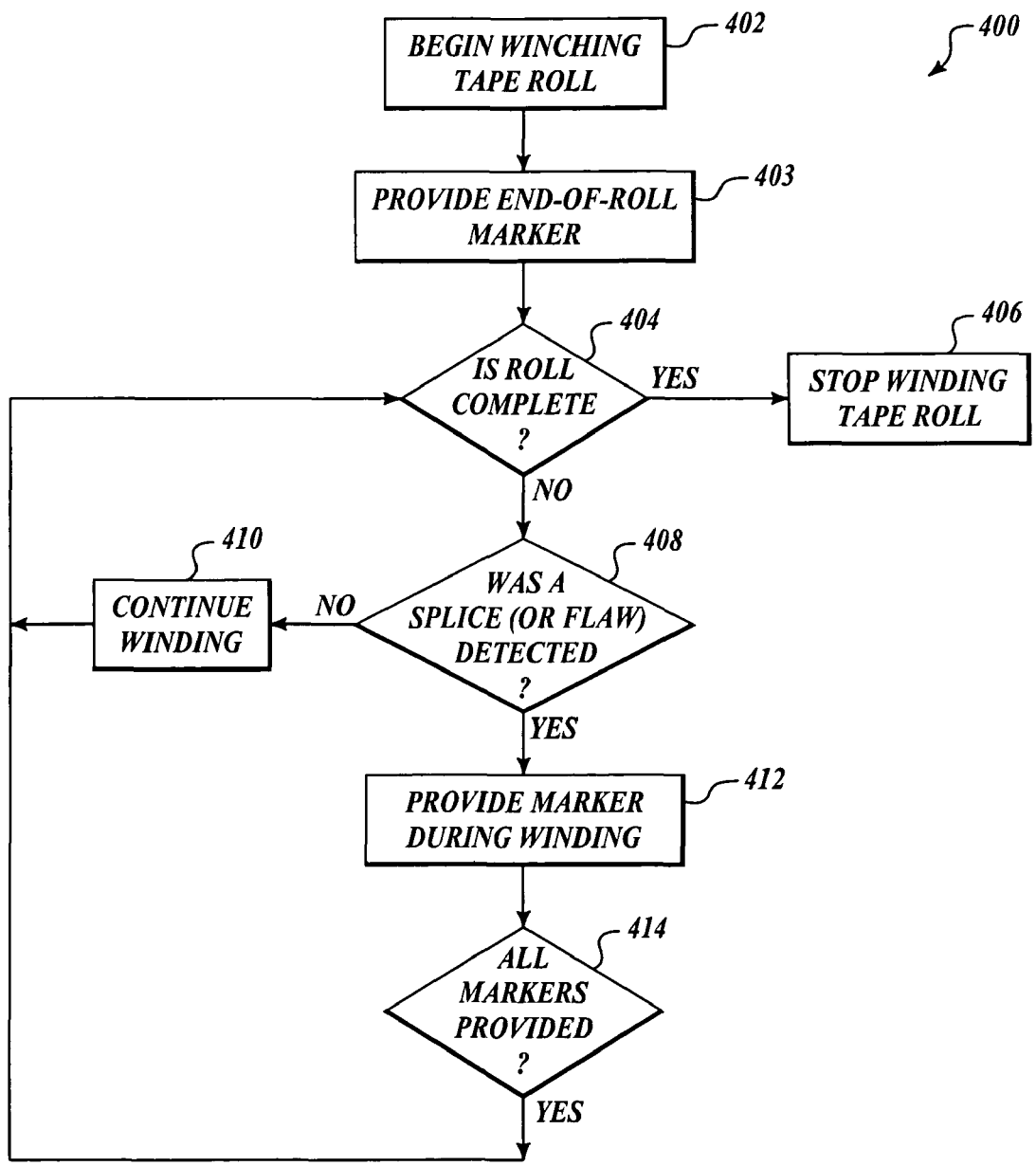
FIG. 5 shows a flow chart of a method for avoiding tape flaws or splices during tape laying in accordance with a further embodiment of the invention.

FIG. 5 shows a flow chart of a method 400 for registering tape splices, flaws and roll ends in accordance with another embodiment of the invention. The method 400 may be used for marking the composite tape with markings at suitable locations in suitable proximity to the locations of splices (or other flaws) and the roll end prior to commencing manufacturing operations which employ the composite tape (e.g. to form a composite component by successively winding the tape onto a mandrel or forming tool). As shown in FIG. 5, the method 400 begins with the winding of the composite tape onto a spool or other suitable holding device at block 402. An end of roll marker is provided at a block 403. At block 404, a determination of whether the tape roll is complete is made. If the tape roll is complete, the winding of the tape roll is stopped at block 406. If the tape roll is not complete, then the method 400 determines whether a splice (or flaw) was detected at block 408. If no splice was detected, then tape winding continues at block 410 and the method 400 then loops back to block 404.

Continuing on from decision block 408, if a splice was detected, the method 400 continues to block 412, where one or more markers is provided at a suitable distance from the splice (or other flaw). The marker(s) may be formed as the tape winds, or alternately, the winding of the tape may be temporarily suspended as the marker(s) is formed. The marker(s) indicates the location of the splice relative to the marker (s). At decision block 414, it is determined whether the desired numbers of markers have been provided. If the desired numbers of markers have not been provided, the method 400 loops back to block 412 to provide more markers. If all the desired markers have been provided, the method 400 loops back to decision block 404 to determine whether the tape roll is complete, and repeats the above-described actions until the tape roll is complete. Although the method 400 shown in FIG. 5 is described in terms of detection of splices, the same method may be used to mark the tape for the presence of flaws or other features of the tape that may be desirable to mark.

Figure 6:
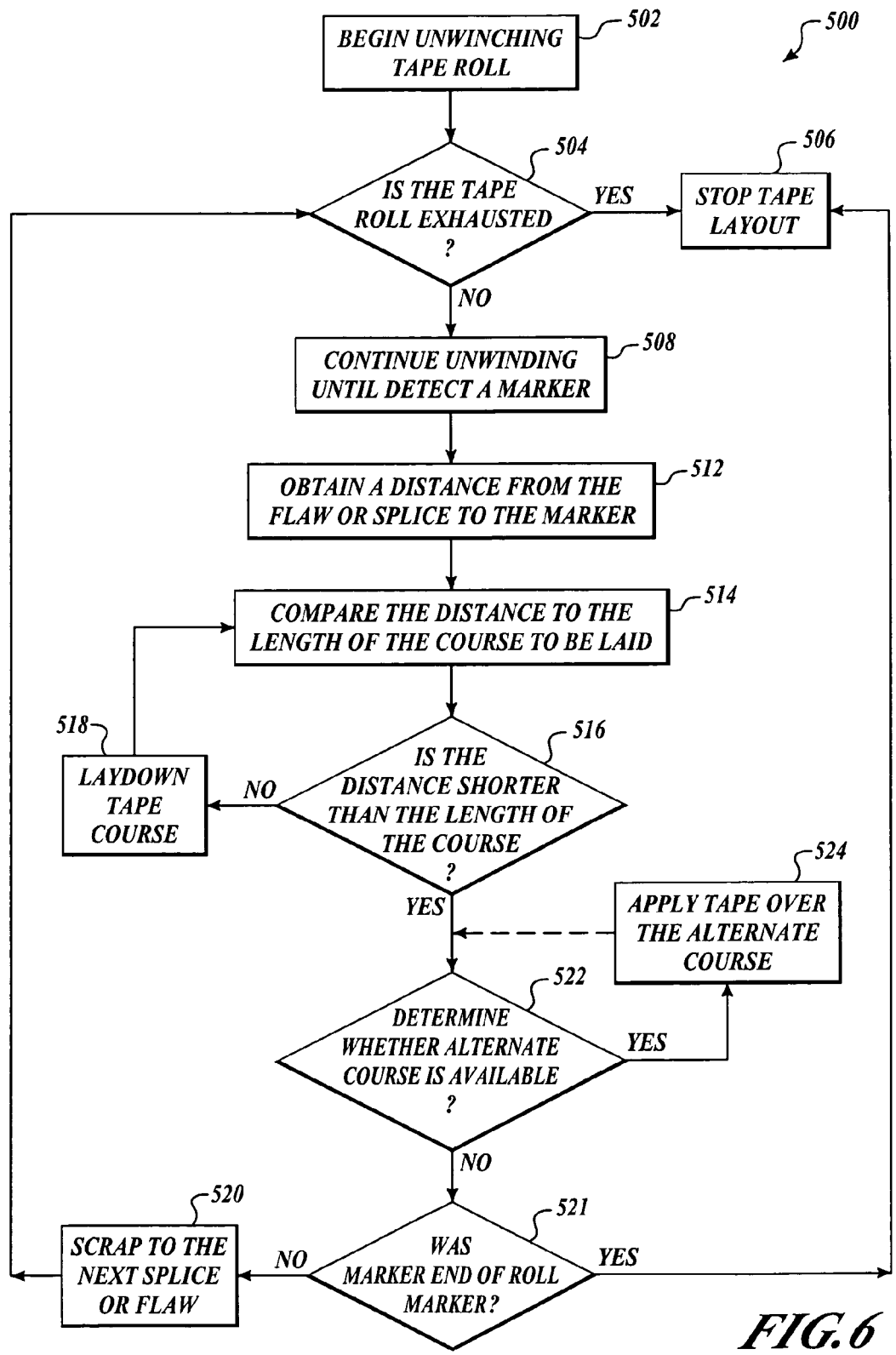
FIG. 6 is an isometric view of a tape with one or more markers indicating a flaw or splice in accordance with still another embodiment of the invention.

FIG. 6 shows a flow chart of a method 500 for avoiding tape flaws or splices during tape laying. The method 500 starts at block 502, where tape unwinding is initiated. A determination is made whether a tape supply is exhausted at decision block 504. If the tape supply is exhausted, then the method 500 terminates at block 506. If tape supply is not exhausted, then at block 508, the tape continues to be unwound (e.g. during application of specified courses of the tape onto a mandrel) and the tape is monitored until a marker is detected by a sensor.

A distance from the flaw or splice to the marker is obtained from the marker at block 512. For example, as described above, different types of markers (e.g. different members of parallel lines) may indicate different distances to the next flaw or splice. At block 514, the distance from the flaw or splice to the marker is compared to the length of the next course to be laid, such as by a controller of an automated tape application machine. If the distance from the flaw or splice to the marker is not shorter than the length of the next course to be laid at decision block 516, then a tape course is laid at block 518, and the method 500 loops back to block 514 to compare the remaining length of tape to the length of the next course to be laid. This loop continues until the logical result of decision block 516 is "yes".

At decision block 516, if the distance to the next flaw or splice or end of roll is shorter than the length of the next course to be laid, then at an optional block 522, the method 500 may determine whether an alternate course in the same layer is available that is shorter than the length of tape available to the next splice or flaw, and if such an alternate course is available, then the tape may be applied along the alternate course at block 524. These optional actions (block 524, 522) may advantageously reduce the amount of tape that is scrapped, further reducing manufacturing costs.

As further shown in FIG. 6, after unwinding the tape on the alternate course (blocked 524), the method 500 will return to the determination block 522 to determine whether another alternate course in the same layer is available that is shorter than the amount of tape remaining to the next splice or flaw or end of roll, and if so, the method 500 may proceed to apply the tape along the other alternate course (block 524). These actions may be iteratively repeated until there are no alternate courses available that are shorter than the amount of tape remaining before the next splice or flaw. At a block 521, the method 500 determines whether the last-detected marker is indicating the end of the tape roll. If it is not the end of the tape roll (i.e. it is a flaw or a splice) then the method 500 proceeds to block 520, wherein the remaining length of tape to the next splice or flaw is scrapped, and then returns to block 504 to repeat the actions described above until the tape supply is exhausted (block 504), and the method terminates (block 506). If the marker was the end of roll marker (block 521), then the method 50 proceeds to stop tape layout (block 506).

It will be appreciated that in some circumstances, the markers for two flaw or splices may overlap, or in other words, the markers for one flaw may be placed so far ahead of it that the markers are actually placed in front of a preceding flaw. For example, depending upon the particular material specifications and anticipated tape courses in the manufacturing operation, the first marker may set a distance to the first flaw/splice, and if a second marker is detected before the first distance has elapsed, then control logic may be developed and programmed into the manufacturing controller to deal with such circumstances.

Figure 7:
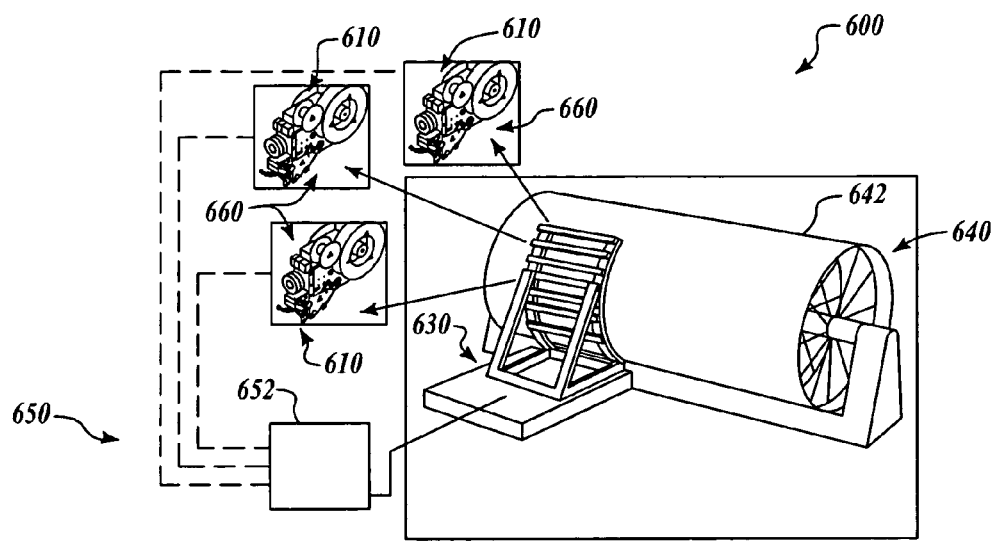
FIG. 7 is an isometric view of a system for manufacturing composite components in accordance with an embodiment of the invention.

Embodiments of systems and methods for avoiding tape flaws or splices in manufacturing operations may be incorporated into a variety of different types of manufacturing systems. For example, FIG. 7 is an isometric view of a system 600 for manufacturing composite components in accordance with an embodiment of the invention. In this embodiment, the system 600 includes a plurality of head assemblies 610 coupled to a translation platform 630 and operatively positioned proximate a forming tool (or template) 640. The translation platform 630 is adapted to systematically move the head assemblies 610 along three-dimensional paths proximate the forming tool 640, and each head assembly 610 is adapted to perform placement and consolidation of a fiber-reinforced composite tape material onto the forming tool 640 to produce a laminated composite workpiece 642, as described more fully below.

Figure 8:
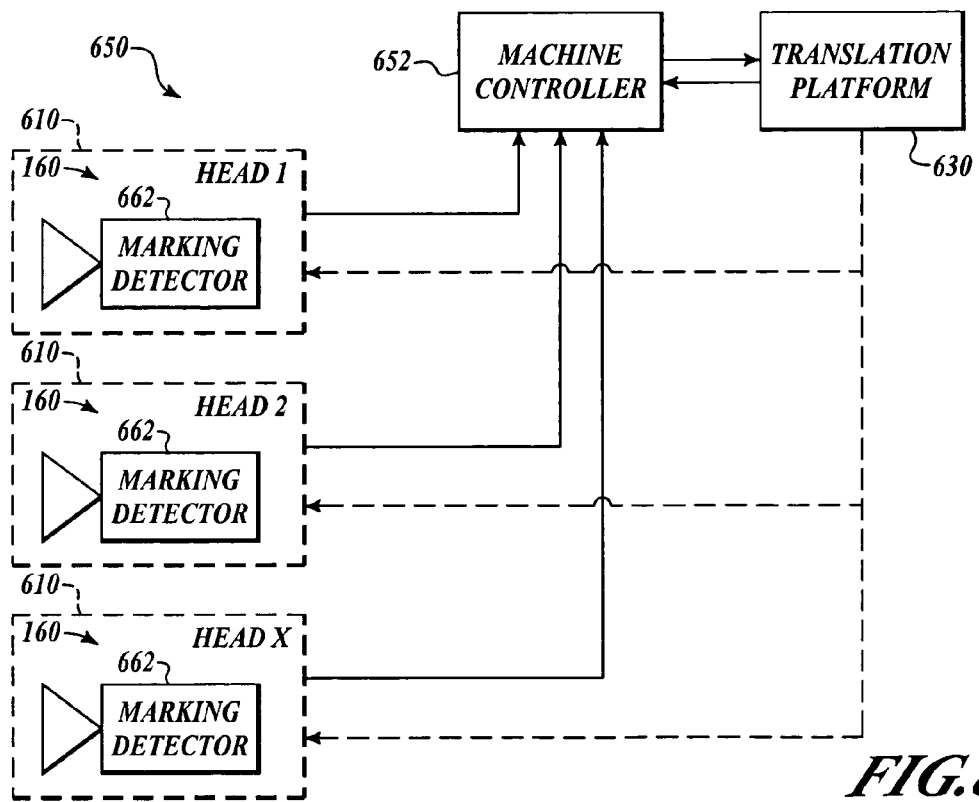
FIG. 8 is a schematic representation of a control system of the manufacturing system of FIG. 7.

FIG. 8 is a schematic representation of a control system 650 of the manufacturing system 100 of FIG. 1. In this embodiment, the control system 150 includes a machine controller 652 operatively coupled to the translation platform 630 and to the head assemblies 610. The machine controller 652 is adapted to implement a control code that transmits control signals to the translation platform 630 and the head assemblies 610. The control signals command the movement and functions of the translation platform 630 and the head assemblies 610, thereby causing automated (or semi-automated) manufacturing of the laminated composite workpiece 642 on the forming tool 640. In the embodiment shown in FIG. 7, the manufacturing system 600 is of a type known as a multi-head tape lamination machine (MHTLM). In one specific embodiment, the system 600 includes three head assemblies 610 for the placement of composite tape, however, in alternate embodiments, any desired number of head assemblies 610 may be employed.

Figure 9:
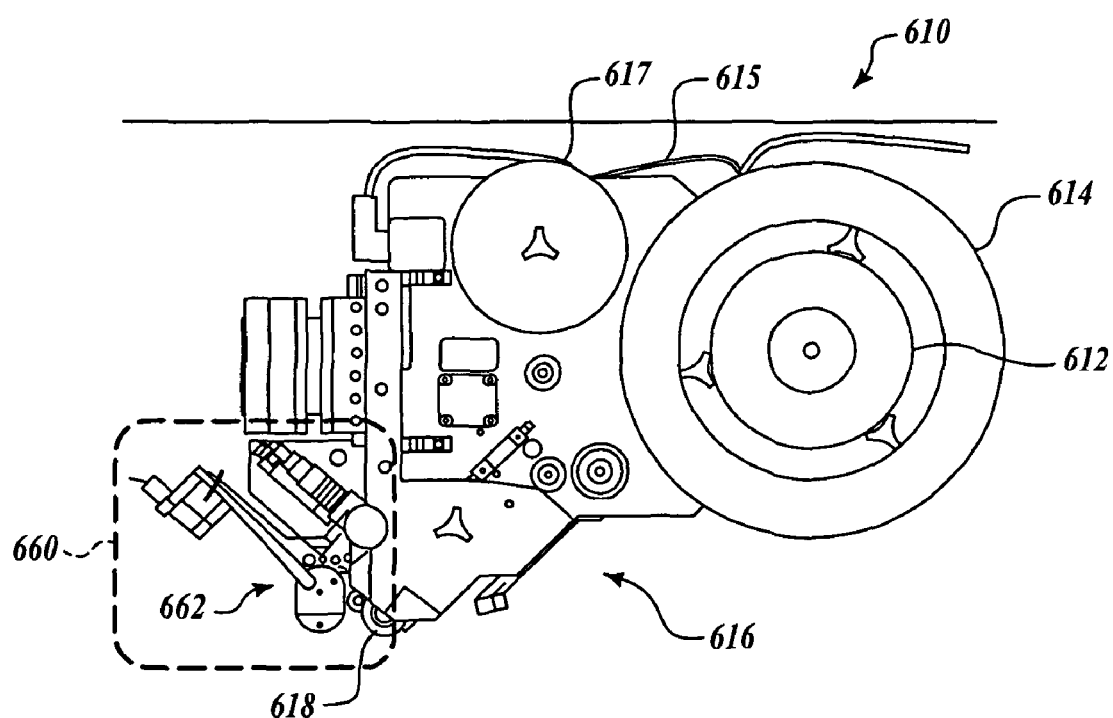
FIG. 9 is an enlarged, side elevational view of a head assembly of the manufacturing system of FIG. 7.

FIG. 9 is a side elevational view of the head assembly 610 of the manufacturing system 600 of FIG. 7. In this embodiment, the head assembly 610 includes a spindle 612 adapted to retain a roll 614 of a fiber-reinforced composite tape 615. The tape 615 may be marked to provide indications of splices or flaws existing in the tape 615 as described more fully above. A feed assembly 616 is adapted to receive, guide, and apply the tape 615 from the roll 614 onto the workpiece 642. More specifically, the feed assembly 616 includes a feed roller 617 that receives the tape 615 from the roll 614, and a compaction roller 618 that applies and compresses the tape 615 onto the workpiece 642. The feed assembly 616 may include a variety of other components (e.g. motors, rollers, guides, sensors, etc.) adapted to cooperatively receive, feed, and guide the tape 615 from the roll 614 to the compaction roller 618, as described more fully, for example, in U.S. Pat. No. 6,799,619 B2 issued to Holmes et al., and U.S. Pat. No. 6,871,684 B2 issued to Engelbart et al.

As further shown in FIGS. 8 and 9, the head assembly 610 further includes a sensor unit 660 adapted to perform in-process inspections of the manufacturing processes (in this case, composite tape application processes) performed by the head assembly 610. Each sensor unit 660 includes a marking detector 662 adapted to detect the markings on the composite tape 615 indicating the distance to the next splice or flaw. As best shown in FIG. 9, the marking detector 662 may be operatively positioned to view a portion of the tape 615 proximate the compaction roller 618, such as prior to the tape 615 being applied and compressed onto the workpiece 142. The sensor unit 660 may be adapted to acquire and analyze signals from the marking detector 662 to determine the presence of markings on the tape 615, or alternately, the signals may be transmitted to the controller 652 (FIG. 8).

As shown in FIG. 8, each sensor unit 660 is coupled to the machine controller 652. Communication between the sensor unit 660 and the controller 652 may be accomplished by standard Ethernet connections, or alternately, by a custom network or server. Communication may also be achieved through a wireless network that utilizes spread spectrum RF to overcome sources of interference in a typical factory environment.

In operation, as the head assemblies 610 are operated to apply the composite tape 615 onto the workpiece 642, the sensor units 660 monitor the tape 615 for the presence of markings. In one embodiment, the sensor units 660 determine whether a marking has been detected on the tape 615, and transmits an indicator signal to the machine controller 652. Alternately, the machine controller 652 may receive raw signals from the sensor units 660 and may perform the determination of whether a marking has been detected. The sensor units 660 (or the controller 652) may use a variety of suitable methods and algorithms for determining whether the markings are present on the tape 615.

Once a marking is detected on the tape 615, the system 600 may take appropriate action, as described above with respect to FIG. 6. For example, the machine controller 652 may perform a check to determine whether the next course of laying the tape 615 for the particular head assembly 610 is longer than the distance to the splice or flaw, and may check for alternate courses that are available that are shorter than the distance to the splice or flaw, as described more fully above.

In one embodiment, when the system 100 detects a flaw or splice marker, the control system 650 may do several things simultaneously (or sequentially): (1) set an operator accessible variable, called U-axis distance to splice position, to match the marker to flaw or splice distance; (2) turn a flaw/splice avoidance checking on, that is, turn on a control logical that begins performing the test that compares course length required by the part program to the distance to splice value; and (3) if no flaw or splices falls within the next course to be laid, continue the sequential lay up process, if a flaw or splice does fall within the length of next course to be laid, then the machine automatically executes a cycle to dispense the tape into the scrap area along the side of the tape laying machine.

In another embodiment of a tape laying machine with the flaw or splice avoidance system, the use of tape that is free from flaws or splices is maximized with further enhancements. Once a flaw marker is detected by the machine sensor, if the next control comparison of the distance to the flaw versus the next course length to be laid finds that a flaw or splice will be encountered within the length of the course, then the control software will initiate a search of the part program. The search will scan all course lengths remaining to be laid within the ply that is in work to find one or more courses of suitable length that can be laid down with the tape length that is available before the flaw or splice. The part program laying sequence would then be automatically reordered by the control to maximize use of tape that is available in front of the splice.

It will be appreciated that a variety of embodiments in accordance with the present invention may be conceived, and that the invention is not limited to the particular embodiments described above or shown in the accompanying figures. For example, letters, numbers, symbols, or other graphics, whether individually or in conjunction, may be used as markers to represent distances to flaws or splices. In one alternate embodiment, barcodes provided on the tape during winding may be used to indicate distances to flaws or splices during winding, and barcode readers may function as sensors to detect the markers during the unwinding of the tape for use.

Furthermore, embodiments of the invention may use a variety of technology to place markers on a composite tape. For example, an embodiment of the invention may use inkjet printing technology to label the tape with one or more markers during winding of the tape into a roll. However, other printing or labeling technology, such as laminating, embossing, stamping, or etching may be used to create markers on the tape. Moreover, although the disclosed embodiments have been described as being adapted to avoidance of tape flaws and splices in the manufacturing of composite structures, it may be appreciated that alternative embodiments of the invention may be used to improve other processes such as tape lamination or fiber placement.

While various embodiments of the invention have been illustrated and described above, many changes can be made without departing from the spirit and scope of the invention. Accordingly, the scope of the invention is not limited by the disclosure of these embodiments. Instead, the invention should be determined entirely by reference to the claims that follow.

What is claimed is:

1. A method comprising:
  detecting a discontinuity in a tape, the discontinuity being at least one of a flaw, splice, cut and roll end; and
  providing one or more markers on the tape in advance of a detected discontinuity in the tape, each marker providing information about location of the detected discontinuity relative to the marker, each marker being positioned to be detectable by a tape laying machine prior to arrival of the detected discontinuity, the one or more markers providing information that allows the tape-laying machine to avoid laying the detected discontinuity.

2. The method of claim 1, wherein the tape is a composite tape including reinforcing fibers.

3. The method of claim 1, wherein the tape includes a composite portion and a removable backing, and wherein providing one or more markers includes providing the markers on the removable backing.

4. The method of claim 1, wherein providing one or more markers includes providing one or more markers at a distance from the detected discontinuity, the distance being greater than a longest required tape course.

5. The method of claim 1, wherein providing one or more markers includes providing a first marker at a furthest distance from the detected discontinuity, and providing a second marker at a closer distance from the detected discontinuity, wherein the markers inform the tape-laying machine that the discontinuity is being approached.

6. The method of claim 5, wherein providing a first marker includes providing a first quantity of approximately parallel lines, and providing a second marker includes providing a second quantity of approximately parallel lines.

7. The method of claim 4, wherein the one or more markers provide information that allows the tape-laying machine to determine whether the next course of laying the tape is longer than the distance to the detected discontinuity or to take alternative actions with a shorter distance of tape.

8. The method of claim 1, wherein the one or more markers are permanently applied to a surface of the tape.

9. The method of claim 1, further comprising winding the tape into a roll.

10. The method of claim 1, wherein the information is machine-encoded by barcode.

11. The method of claim 1, wherein the markers are provided as the tape is being would into a roll.

* * * * *